United States Patent [19]

Drabek

[11] 4,215,122

[45] Jul. 29, 1980

[54] 4-ALKYL- AND 4-ALLYL-MERCAPTO-, -SULFINYL- AND -SULFONYL-METHYL-2-AMINO-6-N,N-DIMETHYLCARBAMOYLOXY-PYRIMIDINES, PROCESSES FOR PRODUCING THEM, COMPOSITIONS CONTAINING THESE PYRIMIDINES, AND THE USE THEREOF FOR CONTROLLING INSECT PESTS

[75] Inventor: Jozef Drabek, Oberwil, Switzerland

[73] Assignee: Ciba-Geigy Corporation, Ardsely, N.Y.

[21] Appl. No.: 54,195

[22] Filed: Jul. 2, 1979

[30] Foreign Application Priority Data

Jul. 7, 1978 [CH] Switzerland .................. 7424/78
Jun. 7, 1979 [CH] Switzerland .................. 5308/79

[51] Int. Cl.$^2$ .................. A01N 9/22; C07D 239/48
[52] U.S. Cl. .................. 424/251; 544/320; 544/321
[58] Field of Search .................. 424/251; 544/320, 321

[56] References Cited

U.S. PATENT DOCUMENTS

| 3,493,574 | 2/1970 | Baranyovits et al. | 544/320 |
| 3,652,566 | 3/1972 | Ghosh et al. | 544/320 |

FOREIGN PATENT DOCUMENTS

| 1181657 | 2/1970 | United Kingdom | 544/320 |
| 1263260 | 2/1972 | United Kingdom | 544/320 |

*Primary Examiner*—Donald G. Daus
*Assistant Examiner*—James H. Turnipseed
*Attorney, Agent, or Firm*—Frederick H. Rabin

[57] ABSTRACT

Compounds of the formula I

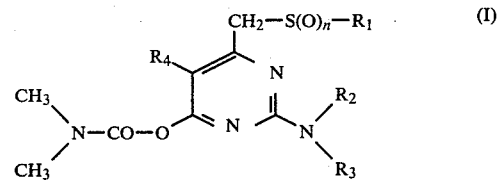

wherein $R_1$ is $C_1$–$C_4$-alkyl or allyl, $R_2$ is hydrogen, methyl or ethyl, $R_3$ is methyl, ethyl or cyclopropyl, $R_4$ is hydrogen or methyl and n is zero, 1 or 2 having valuable insecticidal in particular aphicidal properties.

11 Claims, No Drawings

4-ALKYL- AND 4-ALLYL-MERCAPTO-, -SULFINYL- AND -SULFONYL-METHYL-2-AMINO-6-N,N-DIMETHYLCARBAMOYLOXY-PYRIMIDINES, PROCESSES FOR PRODUCING THEM, COMPOSITIONS CONTAINING THESE PYRIMIDINES, AND THE USE THEREOF FOR CONTROLLING INSECT PESTS

The present invention relates to novel 4-alkyl- and 4-allyl-mercapto-, -sulfinyl- and -sulfonyl-methyl-2-amino-6-N,N-dimethylcarbamoyloxy-pyrimidines which have an action against insect pests, to processes for producing these pyrimidines, to insecticidal compositions containing them as active ingredients, and to processes for the control of insect pests by application of the novel compounds.

2-Aminopyrimidine-6-carbamates having a pesticidal action are known (see G. B. Patent Specification No. 1,181,657). According to the present invention, there are provided novel compounds of this type, which are distinguished by a particularly strongly pronounced action specifically against insects of the order Homoptera, especially of the family Aphididae, and which, by virtue of their advantageous biological properties, are particularly suitable for practical application in the field of pest control.

The 4-alkyl- and 4-allyl-mercapto-, -sulfinyl- and -sulfonyl-methyl-2-amino-6-N,N-dimethylcarbamoyloxypyrimidines according to the invention correspond to the formula I

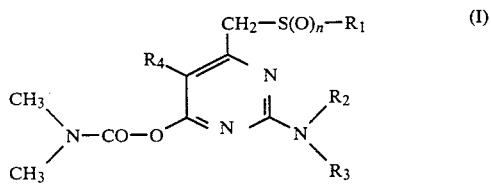

in which
$R_1$ is a $C_1$–$C_4$-alkyl or allyl group,
$R_2$ is a hydrogen atom or a methyl or ethyl group,
$R_3$ is a methyl, ethyl or cyclopropyl group,
$R_4$ is a hydrogen atom or a methyl group, and
n is zero or the integer 1 or 2.

Alkyl groups denoted by $R_1$ can be the methyl, ethyl, n-propyl and i-propyl group, and also the n-, i-, sec- and tert-butyl group.

Preferred types of substituents and combinations of these among each other in the compounds of the formula I are as follows:
(1) for $R_1$: $C_1$–$C_3$-alkyl, especially methyl and ethyl;
(2) for $R_2$: hydrogen or methyl,
 for $R_3$: methyl, and
 for $R_4$: hydrogen;
(3) for n: zero.

The novel compounds of the formula I are advantageously obtained, using methods known per se, by reacting for example
(a) a compound of the formula II

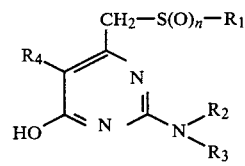

in the presence of a base, with a dimethylcarbamoyl halide, particularly with dimethylcarbamoyl chloride; or
(b) a compound of the formula III

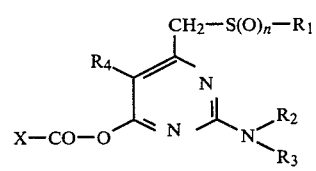

optionally in the presence of a suitable base, with dimethylamine; and in the formulae II and III the symbols $R_1$, $R_2$, $R_3$, $R_4$ and n have the meanings already defined under the formula I, and X is a halogen atom, especially a chlorine atom.

The process (a) is advantageously performed at a temperature of between 20° and 130° C., preferably between 50° and 100° C.; and the process (b) at a temperature of between 50° and 100° C.

Both reactions are performed under normal or slightly elevated pressure, optionally in the presence of a solvent or diluent inert to the reactants. Suitable solvents or diluents are for example: ethers and ethereal compounds, such as diethyl ether, di-isopropyl ether, dioxane and tetrahydrofuran; aromatic hydrocarbons, such as benzene, toluene and xylenes; ketones such as acetone, methyl ethyl ketone and cyclohexanone; nitriles such as acetonitrile; and also dimethylformamide and hexametapol.

Suitable bases for these processes are in particular: tertiary amines such as trialkylamines and dialkylanilines, also hydroxides, oxides, carbonates and bicarbonates of alkali metals and alkaline-earth metals, and also alkali metal alcoholates, such as potassium tert-butylates and sodium methylate.

The starting materials of the formulae II and III are obtainable from known precursors, for example according to the following reaction scheme:

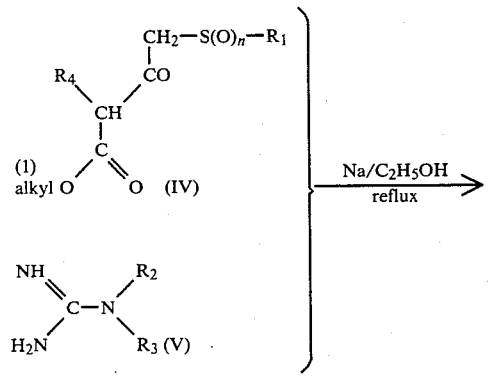

-continued

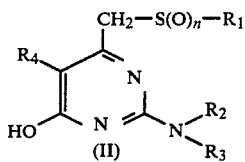

(Compounds of the formula II in which n is the integer 1 or 2 can also be produced by reaction of the appropriate compound of the formula II in which n is zero with an oxidising agent, for example with $H_2O_2$ or an organic peroxide compound or peroxy acid.)

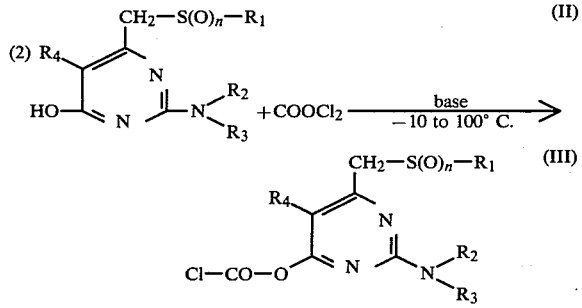

It has now been shown that surprisingly the compounds of the formula I have an excellent action against insect pests, above all against insects of the family Aphididae, which damage plants. It has been found that the compounds according to the invention have both a contact and a systemic action against a wide range of representatives of the stated family (such as Aphis fabae, Aphis craccivora and Myzus persicae), which can be controlled only with the greatest difficulty using known compounds. Furthermore, it has been established that the aphicidal properties mentioned are combined with a toxicity to warm-blooded animals that is advantageously low for application of the novel compounds in the field of agriculture. By virtue of these properties, the compounds of the formula I are particularly suitable for controlling according to the invention insects, especially aphids, in crops of useful plants and ornamental plants, principally in crops of fruit and vegetables.

The insecticidal action of the compounds according to the invention can be considerably broadened and adapted to suit given circumstances by the addition of other insecticides and/or acaricides. Suitable additives are for example: organic phosphorus compounds; nitrophenols and derivatives thereof; formamidines; ureas; pyrethrin-like compounds; carbamates and chlorinated hydrocarbons.

The compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

For application, the compounds of the formula I can be processed into the form of dusts, emulsion concentrates, granulates, dispersions, sprays, solutions or suspensions, using customary methods of formulation which form part of the common knowledge related to application techniques.

The compositions according to the invention are produced in a manner known per se by the intimate mixing and/or grinding of the active substances of the formula I with suitable carriers, optionally with the addition of dispersing agents or solvents which are inert to the active substances. The active substances (compounds of the formula I) can be obtained and used in the following forms:

solid preparations: dusts, scattering agents, granules (coated granules, impregnated granules and homogeneous granules);

liquid preparations:
 (a) water-dispersible wettable powders, pastes and emulsions;
 (b) solutions.

The content of active substance (compound of the formula I) in the compositions described above is between 0.1 and 95%; it is to be mentioned in this respect that with application from an aeroplane or from other suitable application devices, also higher concentrations may be used.

The active substances of the formula I can be formulated for example as follows:

Dusts

The following substances are used to produce (a) a 5% dust and (b) a 2% dust:
 (a)
  5 parts of active substance,
  95 parts of talcum; and
 (b)
  2 parts of active substance,
  1 part of highly dispersed silicic acid, and
  97 parts of talcum.

The active substances are mixed and ground with the carriers.

Granulate

The following ingredients are used to produce a 5% granulate:
 5 parts of active substance,
 0.25 part of epichlorohydrin,
 0.25 part of cetyl polyglycol ether,
 3.50 parts of polyethylene glycol, and
 91 parts of kaolin (particle size 0.3–0.8 mm).

The active substance is mixed with epichlorohydrin and dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:
 (a)
  40 parts of active substance,
  5 parts of sodium lignin sulfonate,
  1 part of sodium dibutyl-naphthalene sulfonate, and
  54 parts of silicic acid;
 (b)
  25 parts of active substance,
  4.5 parts of calcium lignin sulfonate,
  1.9 parts of Champagne chalk/hydroxyethyl cellulose mixture (1:1),
  1.5 parts of sodium dibutyl-naphthalene sulfonate,
  19.5 parts of silicic acid,
  19.5 parts of Champagne chalk, and 28.1 parts of kaolin;

(c)
- 25 parts of active substance,
- 2.5 parts of isooctylphenoxy-polyoxyethylene-ethanol,
- 1.7 parts of Champagne chalk/hydroxyethyl cellulose mixture (1:1),
- 8.3 parts of sodium aluminium silicate,
- 16.5 parts of kieselguhr, and
- 46 parts of kaolin; and (d)
- 10 parts of active substance,
- 3 parts of a mixture of the sodium salts of saturated fatty alcohol sulfates,
- 5 parts of naphthalenesulfonic acid/formaldehyde condensate, and
- 82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrate

The following substances are used to produce (a) a 10% emulsifiable concentrate, (b) a 25% emulsifiable concentrate and (c) a 50% emulsifiable concentrate:

(a)
- 10 parts of active substance,
- 3.4 parts of epoxidised vegetable oil,
- 3.4 parts of a combination emulsifier consisting of fatty alcohol polyglycol ether and alkylarylsulfonate calcium salt,
- 40 parts of dimethylformamide, and
- 43.2 parts of xylene;

(b)
- 25 parts of active substance,
- 2.5 parts of epoxidised vegetable oil,
- 10 parts of alkylarylsulfonate/fatty alcohol polyglycol ether mixture,
- 5 parts of dimethylformamide, and
- 57.5 parts of xylene; and (c)
- 50 parts of active substance,
- 4.2 parts of tributylphenol-polyglycol ether,
- 5.8 parts of calcium-dodecylbenzenesulfonate,
- 20 parts of cyclohexanone, and
- 20 parts of xylene.

Emulsions of the required concentration can be prepared from these concentrates by dilution with water.

Spray

The following constituents are used to produce (a) a 5% spray and (b) a 95% spray:

(a)
- 5 parts of active substance,
- 1 part of epichlorohydrin, and
- 94 parts of ligroin (boiling limits 160°–190° C.); and (b)
- 95 parts of active substance, and
- 5 parts of epichlorohydrin.

The Examples which follow serve to further illustrate the invention.

EXAMPLE 1

Production of 2-dimethylamino-4-ethylmercaptomethyl-6-N,N-dimethylcarbamoyloxy-pyrimidine (a) Production of the starting material: 2-dimethylamino-4-ethylmercaptomethyl-6-hydroxy-pyrimidine.

47.9 g of dimethylguanidine sulfate was added in portions, at room temperature, to a solution of 8.1 g of sodium in 300 ml of abs. ethanol. The mixture obtained was stirred for one hour at room temperature, and was subsequently refluxed for a further 30 minutes. After cooling, there was added dropwise 62.0 g of γ-ethylmercaptoacetoacetic acid methyl ester, and the resulting reaction mixture was refluxed for 24 hours. The reaction mixture obtained was cooled and subsequently poured into ice/water, and the pH was adjusted to 7. After extraction of the reaction mixture with methylene chloride, the organic phase was dried over Na$_2$SO$_4$; the solvent was then distilled off, and the resulting crude product was recrystallised from water to thus yield 2-dimethylamino-4-ethylmercaptomethyl-6-hydroxy-pyrimidine in the form of colourless crystals having a melting point of 119°–121° C.

(b) Production of 2-dimethylamino-4-mercaptomethyl-6-N,N-dimethyl-carbamoyloxy-pyrimidine.

9.7 g of K$_2$CO$_3$ and 0.4 ml of triethylamine were added to a solution of 14.9 g of 2-dimethylamino-4-ethylmercaptomethyl-6-hydroxy-pyrimidine in 100 ml of methyl ethyl ketone. After the mixture had been stirred for 2 hours under reflux, 7.5 g of dimethylcarbamoyl chloride was added dropwise with stirring, and the reaction mixture obtained was subsequently refluxed for 8 hours. The resulting mixture on cooling was filtered under suction and the filtrate was concentrated by evaporation; the residue was then taken up in ether, washed twice with water, dried over Na$_2$SO$_4$, and afterwards concentrated by evaporation. There was obtained in this manner 2-dimethylamino-4-ethylmercaptomethyl-6-N,N-dimethylcarbamoyl-pyrimidine of the formula

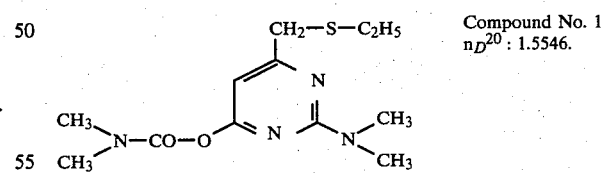

Compound No. 1
$n_D^{20}$: 1.5546.

Also the following compounds of the formula I can be produced by production processes analogous to those described above:

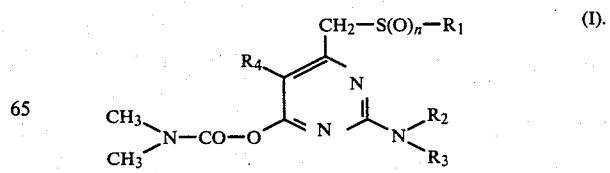

| Comp. No. | R$_1$ | R$_2$ | R$_3$ | R$_4$ | n | Physical data |
|---|---|---|---|---|---|---|
| 2 | CH$_3$ | CH$_3$ | CH$_3$ | H | 0 | n$_D^{20}$: 1,5592 |
| 3 | CH$_3$ | CH$_3$ | CH$_3$ | H | 1 | m.p.: 75°–77° C. |
| 4 | CH$_3$ | CH$_3$ | CH$_3$ | H | 2 | |
| 5 | CH$_3$ | CH$_3$ | CH$_3$ | CH$_3$ | 0 | m.p.: 90°–92° C. |
| 6 | CH$_3$ | H | CH$_3$ | H | 0 | m.p.: 88°–90° C. |
| 7 | C$_2$H$_5$ | H | ▷ | H | 0 | n$_D^{34}$: 1,5564 |
| 8 | nC$_3$H$_7$ | CH$_3$ | CH$_3$ | H | 0 | n$_D^{20}$: 1,5499 |
| 9 | n-C$_4$H$_9$ | CH$_3$ | CH$_3$ | H | 0 | |
| 10 | CH$_3$ | C$_2$H$_5$ | C$_2$H$_5$ | H | 0 | |
| 11 | CH$_2$=CH—CH$_2$— | CH$_3$ | CH$_3$ | H | 0 | |

EXAMPLE 2

Insecticidal contact action: *Aphis craccivora* and *Myzus persicae*

Plants (*Vicia faba*) grown in pots were each infested, before the commencement of the test, with about 200 individuals of the species *Aphis fabae* and *Myzus persicae*, respectively. Twenty-four hours later, the plants treated in this manner were sprayed until dripping wet with a solution containing 200 and 100 ppm, respectively, of the compound to be tested. Two plants were used per test compound and per concentration, and an evaluation of the attained degree of destruction of the insects was made after a further 24 hours.

Compounds according to Example 1 exhibited in the above test a favourable action against insects of the species *A phis craccivora* and *Myzus persicae*.

EXAMPLE 3

Insecticidal action (systemic): *Aphis craccivora*

Rooted bean plants were transplanted into pots containing 600 ccm of soil, and subsequently 50 ml of a solution of the compound to be tested (obtained from a 25% wettable powder) at a concentration of 50 ppm and 10 ppm, respectively, was poured directly onto the soil. After 24 hours, lice of the species *Aphis craccivora* were settled onto the parts of the plant above the soil, and a plastics cylinder was put over each plant in order to protect the lice from a possible contact or gas effect of the test substance.

The evaluation of the achieved destruction of lice was made after 48 and 72 hours, respectively, after commencement of the test. Two plants, each in a separate pot, were used per concentration dose of test substance. The test was carried out at 25° C. with 70% relative humidity.

Compounds according to Example 1 exhibited in the above test a good systemic action against insects of the species *Aphis craccivora*.

What is claimed is:

1. A compound of the formula I

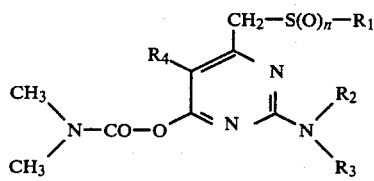

wherein R$_1$ is C$_1$–C$_4$-alkyl or allyl, R$_2$ is hydrogen, methyl, or ethyl, R$_3$ is methyl, ethyl or cyclopropyl, R$_4$ is hydrogen or methyl and n is zero or the integer 1 or 2.

2. A compound as claimed in claim 1, wherein R$_1$ is C$_1$–C$_3$-alkyl.

3. A compound as claimed in claim 2, wherein R$_1$ is methyl or ethyl.

4. A compound as claimed in claim 3, wherein n is zero.

5. A compound as claimed in any one of claims 2 to 4 wherein R$_2$ is hydrogen or methyl, R$_3$ is methyl and R$_4$ is hydrogen.

6. A compound as claimed in claim 1 of the formula

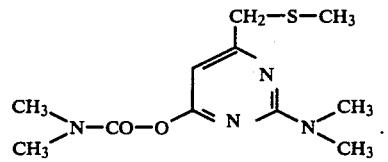

7. A compound as claimed in claim 1 of the formula

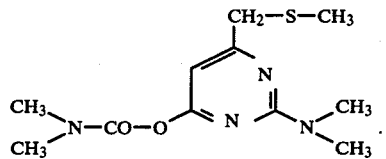

8. A compound as claimed in claim 1 of the formula

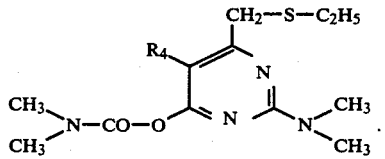

9. An insecticidal composition comprising an insecticidally effective amount of a compound as claimed in claim 1, together with an inert, solid or liquid diluent or carrier therefor.

10. A method of controlling insect pests at a locus which method comprises applying to said locus a pesticidally effective amount of a compound as claimed in claim 1.

11. A method as claimed in claim 8 wherein the insect pests are of the family Aphididae.

* * * * *